US012806059B2

(12) United States Patent
Madden et al.

(10) Patent No.: US 12,806,059 B2
(45) Date of Patent: Nov. 24, 2026

(54) SACROILIAC ORTHOSIS

(71) Applicant: DJO, LLC, Carlsbad, CA (US)

(72) Inventors: Dave Madden, Carlsbad, CA (US); Jeremy Nathanson, Vista, CA (US)

(73) Assignee: DJO, LLC, Carlsbad, CA (US)

( * ) Notice: Subject to any disclaimer, the term of this patent is extended or adjusted under 35 U.S.C. 154(b) by 524 days.

(21) Appl. No.: 18/111,199

(22) Filed: Feb. 17, 2023

(65) Prior Publication Data

US 2023/0201020 A1 Jun. 29, 2023

Related U.S. Application Data

(63) Continuation of application No. PCT/US2021/045487, filed on Aug. 11, 2021.

(60) Provisional application No. 63/067,764, filed on Aug. 19, 2020.

(51) Int. Cl.
*A61F 5/02* (2006.01)

(52) U.S. Cl.
CPC .................................... *A61F 5/028* (2013.01)

(58) Field of Classification Search
CPC . A61F 5/02–03; A61F 5/0193; A61F 5/23–34
USPC ............................................ 602/19; 128/876
See application file for complete search history.

(56) References Cited

U.S. PATENT DOCUMENTS 4,572,167 A 2/1986 Brunswick
7,765,619 B2 8/2010 Jaccard
8,057,417 B2 11/2011 Imai
8,182,438 B2 5/2012 Rumsey
8,920,353 B2 12/2014 Tinshon et al.
(Continued)

FOREIGN PATENT DOCUMENTS

EP 1901685 B1 11/2009
EP 2916673 B1 10/2018
(Continued)

OTHER PUBLICATIONS

International Preliminary Report on Patentability received for WO Patent Application Serial No. PCT/US2021/045487 dated Mar. 2, 2023, 07 pages.
(Continued)

*Primary Examiner* — Keri J Nelson
*Assistant Examiner* — Seth R. Brown
(74) *Attorney, Agent, or Firm* — Veros Legal Solutions, LLP

(57) ABSTRACT

An orthopedic sacroiliac brace is provided. The brace includes a belt portion including a first posterior sacral panel coupled to the belt portion and configured to be disposed directly posterior of a first posterior side of an ilium of a user, and a second posterior sacral panel coupled to the belt portion and configured to be disposed directly posterior of a second posterior side of the ilium. Adjustably tightening the belt portion around the user causes the first and second posterior sacral panels to apply respective anterior forces to the first and second posterior sides of the ilium, thereby providing adjustable stabilizing support, compression and/or alignment to a sacroiliac joint of the user. Brace can also include an anterior abdominal panel configured to be disposed against an anterior portion of an abdomen of the user and coupled to the belt portion. Related methods of use and manufacture are also provided.

14 Claims, 10 Drawing Sheets

(56) References Cited

U.S. PATENT DOCUMENTS

| | | | | |
|---|---|---|---|---|
| 8,926,537 | B2 | 1/2015 | Ingimundarson et al. | |
| 8,945,033 | B1 * | 2/2015 | Guldalian | A61F 5/028 602/5 |
| 9,402,758 | B2 | 8/2016 | Matsuo et al. | |
| 9,655,761 | B2 * | 5/2017 | Joseph | A61F 5/028 |
| 9,713,545 | B2 | 7/2017 | Hinshon et al. | |
| 9,949,860 | B2 | 4/2018 | Garth et al. | |
| 10,517,749 | B2 * | 12/2019 | Joseph | A61F 5/028 |
| 11,484,429 | B2 * | 11/2022 | Joseph | A61F 5/028 |
| 2010/0217167 | A1 * | 8/2010 | Ingimundarson | A61F 5/028 602/19 |
| 2013/0030338 | A1 * | 1/2013 | Hinshon | A61F 5/028 602/19 |
| 2014/0081189 | A1 * | 3/2014 | Ingimundarson | A61F 5/028 602/19 |
| 2014/0135672 | A1 * | 5/2014 | Joseph | A61F 5/028 602/19 |
| 2014/0188023 | A1 * | 7/2014 | Modglin | A61F 5/028 602/19 |
| 2014/0221893 | A1 * | 8/2014 | Modglin | A61F 5/028 602/19 |
| 2014/0303536 | A1 * | 10/2014 | Guldalian | A61F 5/028 602/19 |
| 2015/0126918 | A1 * | 5/2015 | Modglin | A61F 5/028 602/19 |
| 2015/0250634 | A1 * | 9/2015 | Garth | A61F 5/028 602/19 |
| 2016/0324678 | A1 | 11/2016 | Ingimundarson et al. | |
| 2018/0049904 | A1 | 2/2018 | Ingimundarson et al. | |
| 2018/0085244 | A1 * | 3/2018 | Burke | A61F 13/01038 |
| 2018/0221189 | A1 | 8/2018 | Garth et al. | |
| 2019/0262163 | A1 | 8/2019 | Burke et al. | |
| 2019/0374366 | A1 | 12/2019 | Ohliger | |
| 2020/0237547 | A1 | 7/2020 | Joseph et al. | |

FOREIGN PATENT DOCUMENTS

| | | | |
|---|---|---|---|
| EP | 2596711 | B1 | 1/2019 |
| EP | 2938299 | B1 | 6/2019 |
| EP | 3113730 | B1 | 4/2020 |
| EP | 4199868 | B1 | 8/2025 |
| WO | 2009054354 | A1 | 4/2009 |
| WO | 2018173098 | A1 | 9/2018 |
| WO | 2022039987 | A1 | 2/2022 |

OTHER PUBLICATIONS

Intend to Grant mailed on Mar. 4, 2025 in EP 21765778.2.
Notice of Allowance mailed on Dec. 18, 2025 in CA 3,189,901.
Office Action mailed on Jun. 12, 2024 in CA 3189901.
Office Action mailed on Oct. 9, 2025 in MX MX/a/2023/002079.

* cited by examiner

SACROILIAC ORTHOSIS

CROSS-REFERENCE TO RELATED APPLICATIONS

This application is a Continuation of PCT Application No. PCT/US2021/045487, filed Aug. 11, 2021, which claims the benefit of U.S. Application No. 63/067,764, filed Aug. 19, 2020, the entire contents of each are hereby incorporated by reference in their entirety herein.

BACKGROUND

The present disclosure relates to sacroiliac orthosis, methods of using the same to provide pelvic sacral support, and/or methods of manufacturing such orthoses.

A sacroiliac belt can be worn around the upper hips of an individual to exert a compressive force around the pelvic girdle and to stabilize and reduce strain in the sacroiliac joint. There are a number of commercially available orthoses intended to stabilize and immobilize the lumbar and sacral region of the body for use in the treatment of lower back pain. Such devices are often employed for treating pain associated with conditions such as lumbar sprain, spinal stenosis, disc herniation, as well as pain and discomfort associated with degenerative spinal disorders. Nevertheless, many of these devices do not fully address spinal concerns.

Due to the variability of individuals in terms of size, weight and anatomy, ensuring optimal fit and comfort can be challenging. There remains a need for sacroiliac belts that can be easily adjusted to ensure proper fit, customizable support, and requisite immobilization to the necessary regions of the back when the device is worn.

One type of sacroiliac belt disclosed in the art includes an elastic inner part that wraps around the user's hips and a non-elastic outer part that encircles the inner pan to establish an overall non-elastic sacroiliac belt. U.S. Pat. No. 4,572,167 discloses a sacroiliac belt, with elastic panels and a non-elastic cinch strap encircling the panels. Another sacroiliac belt of this type includes elastic Neoprene to wrap around the user's hips and non-elastic Nylon to wrap around the Neoprene. However, this sacroiliac belt is not recommended for wearing directly against the skin because the closed-cell structure of Neoprene causes heat build-up which can lead to skin irritation.

Another type of prior sacroiliac belt is generally elastic, which allows good compression of the sacroiliac joint. However, while such elastic sacroiliac belts can provide a certain measure of lumbar support, such elastic sacroiliac belts will not typically provide sufficient compression to specifically limit motion of the sacroiliac, joint below its very low, normal range of motion, e.g., approximately 3 degrees. In this way, an overall elastic sacroiliac belt can give a false sense of security to the user because the actions that open the sacroiliac joint, i.e., bending, lifting, and twisting, can force the joint open beyond its normal range of motion even with such elastic sacroiliac belts in place. In other words, elastic sacroiliac belts do not create a stop point at the end of the normal range of motion of the sacroiliac joint. As ligaments are essentially non-elastic, movement of the sacroiliac joint beyond its normal range will stress the ligaments and potentially re-injure the joint.

U.S. Patent Publication No. 2019/0374366A1 describes a sacroiliac belt with internal distractions. The design includes a belt having an inner belt configured to encircle a waist portion of a user. The inner belt has a first end, a second end, and a length that extends from the first end to the second end.

Notably, the belt also includes a plurality of pockets coupled to the internal side of the inner belt, configured to receive distraction devices.

U.S. Pat. No. 9,402,758 describes a supporter constructed from a single sheet of knitted fabric.

Accordingly, a need exists for improved sacroiliac belts that provide sufficient support and stabilization to one or more sacroiliac joints of a wearer. Additionally, there remains a need for adjustable belts to enhance the fit of such belts on the wearer.

SUMMARY

In some embodiments, an orthopedic sacroiliac brace is provided. The brace includes a belt portion. The brace includes a first posterior sacral panel coupled to the belt portion and configured to be disposed directly posterior of a first posterior side of an ilium of a user. The brace includes a second posterior sacral panel coupled to the belt portion and configured to be disposed directly posterior of a second posterior side of the ilium. Adjustably tightening the belt portion around the user causes the first and second posterior sacral panels to apply respective anterior forces to the first and second posterior sides of the ilium, thereby providing adjustable stabilizing support, compression and/or alignment to a sacroiliac joint of the user.

In some other embodiments, a method of using an orthopedic sacroiliac brace for to providing pelvic sacral support is provided. The method includes disposing a belt portion of the brace around a waist of a user such that a first posterior sacral panel, coupled to the belt portion, is disposed directly posterior of a first posterior side of an ilium of the user, and a second posterior sacral panel, coupled to the belt portion, is disposed directly posterior of a second posterior side of the ilium. The method includes, adjustably tightening the belt portion around the waist of the user such that the first and second posterior sacral panels are caused to apply respective anterior forces to the first and second posterior sides of the ilium, thereby providing adjustable stabilizing support, compression and/or alignment to a sacroiliac joint of the user.

In some other embodiments, a method of manufacturing an orthopedic sacroiliac brace is provided. The method includes providing a belt portion. The method includes coupling a first posterior sacral panel to the belt portion and a second posterior sacral panel to the belt portion such that: (A) the first posterior sacral panel is configured to be disposed directly posterior of a first posterior side of an ilium of a user when the brace is worn, (B) the second posterior sacral panel is configured to be disposed directly posterior of a second posterior side of the ilium of the user when the brace is worn, and (C) adjustably tightening the belt portion around the user causes the first and second posterior sacral panels to apply respective anterior forces to the first and second posterior sides of the ilium, thereby providing adjustable stabilizing support, compression and/or alignment to a sacroiliac joint of the user.

BRIEF DESCRIPTION OF THE DRAWINGS

A more complete appreciation of the subject matter of the present disclosure and of the various advantages thereof can be realized by reference to the following detailed description in which reference is made to the accompanying drawings in which.

DETAILED DESCRIPTION

Figure 1:
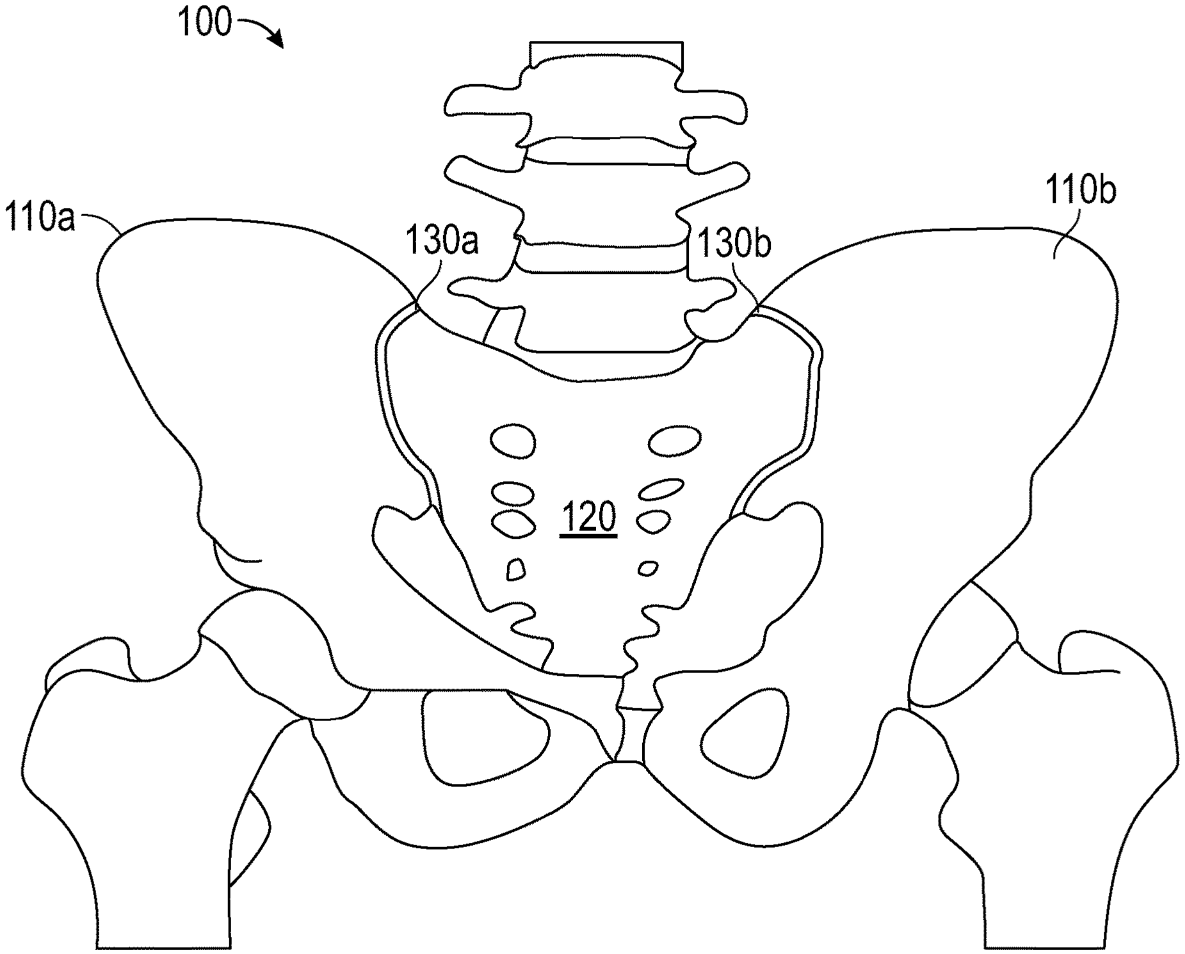
FIG. 1 illustrates an anatomy of a hip, pelvis and lower back of a human body, in accordance with some embodiments.

The present disclosure relates to sacroiliac orthoses, methods of using such orthoses to provide pelvic sacral support, and associated methods of manufacturing such orthoses.

General Interpretive Principles

Various aspects of the novel systems, apparatuses, and methods are described more fully hereinafter with reference to the accompanying drawings. The teachings disclosure may, however, be embodied in many different forms and should not be construed as limited to any specific structure or function presented throughout this disclosure. Rather, these aspects are provided so that this disclosure will be thorough and complete, and will fully convey the scope of the disclosure to those skilled in the art. Based on the teachings herein one skilled in the art should appreciate that the scope of the disclosure is intended to cover any aspect of the novel systems, apparatuses, and methods disclosed herein, whether implemented independently of or combined with any other aspect of the disclosure. For example, a system or an apparatus may be implemented, or a method may be practiced using any one or more of the aspects set forth herein. In addition, the scope of the disclosure is intended to cover such a system, apparatus or method which is practiced using other structure, functionality, or structure and functionality in addition to or other than the various aspects of the disclosure set forth herein. It should be understood that any aspect disclosed herein may be set forth in one or more elements of a claim. Although some benefits and advantages of the preferred aspects are mentioned, the scope of the disclosure is not intended to be limited to particular benefits, uses, or objectives. The detailed description and drawings are merely illustrative of the disclosure rather than limiting, the scope of the disclosure being defined by the appended claims and equivalents thereof.

With respect to the use of plural vs. singular terms herein, those having skill in the art can translate from the plural to the singular and/or from the singular to the plural as is appropriate to the context and/or application. The various singular/plural permutations may be expressly set forth herein for sake of clarity.

When describing an absolute value of a characteristic or property of a thing or act described herein, the terms "substantial," "substantially," "essentially," "approximately," and/or other terms or phrases of degree may be used without the specific recitation of a numerical range. When applied to a characteristic or property of a thing or act described herein, these terms refer to a range of the characteristic or property that is consistent with providing a desired function associated with that characteristic or property.

In those cases where a single numerical value is given for a characteristic or property, it is intended to be interpreted as at least covering deviations of that value within one significant digit of the numerical value given.

If a numerical value or range of numerical values is provided to define a characteristic or property of a thing or act described herein, whether or not the value or range is qualified with a term of degree, a specific method of measuring the characteristic or property may be defined herein as well. In the event no specific method of measuring the characteristic or property is defined herein, and there are different generally accepted methods of measurement for the characteristic or property, then the measurement method should be interpreted as the method of measurement that would most likely be adopted by one of ordinary skill in the art given the description and context of the characteristic or property. In the further event there is more than one method of measurement that is equally likely to be adopted by one of ordinary skill in the art to measure the characteristic or property, the value or range of values should be interpreted as being met regardless of which method of measurement is chosen.

It will be understood by those within the art that terms used herein, and especially in the appended claims (e.g., bodies of the appended claims) are intended as "open" terms unless specifically indicated otherwise (e.g., the term "including" should be interpreted as "including but not limited to," the term "having" should be interpreted as "having at least," the term "includes" should be interpreted as "includes but is not limited to," etc.).

It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations. In addition, even if a specific number of an introduced claim recitation is explicitly recited, those skilled in the art will recognize that such recitation should typically be interpreted to mean at least the recited number (e.g., the bare recitation of "two recitations," without other modifiers, typically means at least two recitations, or two or more recitations).

In those instances where a convention analogous to "at least one of A, B, and C" is used, such a construction would include systems that have A alone, B alone, C alone, A and B together without C, A and C together without B, B and C together without A, as well as A, B, and C together. It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include A without B, B without A, as well as A and B together."

Various modifications to the implementations described in this disclosure can be readily apparent to those skilled in the art, and generic principles defined herein can be applied to other implementations without departing from the spirit or scope of this disclosure. Thus, the disclosure is not intended to be limited to the implementations shown herein but is to be accorded the widest scope consistent with the claims, the principles and the novel features disclosed herein. The word "exemplary" is used exclusively herein to mean "serving as an example, instance, or illustration." Any implementation described herein as "exemplary" is not necessarily to be construed as preferred or advantageous over other implementations.

Certain features that are described in this specification in the context of separate implementations also can be implemented in combination in a single implementation. Conversely, various features that are described in the context of a single implementation also can be implemented in multiple implementations separately or in any suitable sub-combination. Moreover, although features can be described above as acting in certain combinations and even initially claimed as such, one or more features from a claimed combination can in some cases be excised from the combination, and the claimed combination can be directed to a sub-combination or variation of a sub-combination.

Several Example Embodiments

FIG. 1 illustrates an anatomy of a hip, pelvis and lower back of a human body, in accordance with some embodiments. For example, a hip 100 is illustrated, comprising a sacrum 120 (forming a bottom of the backbone) and an ilium having a first posterior side 110*a* disposed immediately adjacent a first side of sacrum 120 and a second posterior side 110*b* disposed immediately adjacent a second side of sacrum 120 opposite the first side of sacrum 120. A first sacroiliac (SI) joint 130*a* is formed between first posterior side 110*a* of ilium and the immediately adjacent first side of sacrum 120 and a second SI joint 130*b* is formed between second posterior side 110*b* of the ilium and the immediately adjacent second side of sacrum 120.

Actions that can open first and/or second SI joint(s) 130*a*, 130*b* include bending, lifting, and/or twisting motions of the low back. However, the normal range of motion of first and second SI joints 130*a*, 130*b* (e.g., a range of motion of first and/or second sides 110*a*, 110*b* of ilium with respect to the corresponding immediately adjacent first and/or second sides of sacrum 120) is very low, e.g., approximately 3°. Accordingly, where such actions force first and/or second SI joint 130*a*, 130*b* open beyond their normal range(s) of motion, stress or damage to, and/or injury or reinjury of, the ligaments holding the first and/or second SI joints 130*a*. 130*b* together can occur. Accordingly, a need exists for a sacral orthosis, brace and/or belt configured to provide support and/or stabilization specifically to first and/or second SI joints 130*a*, 130*b*.

Accordingly, this disclosure contemplates sacroiliac orthoses, braces or belts having one or more removable and/or movable panels disposed such that they are configured to create pressure in the coronal plane of the hip/pelvis region as circumferential pressure is applied to the orthosis, brace and/or belt. This pressure compresses the tissues of the hip and, thereby, stabilizes and maintains proper alignment of one or both of SI joints 130*a*, 130*b* in that coronal plane. Inventive embodiments described herein benefit, in part, from a surprising discovery that sacroiliac orthoses, braces and/or belts, as described herein, provide a unique level of support and/or stabilization specifically to first and/or second SI joints 130*a*, 130*b*.

Several example embodiments of a sacroiliac orthosis, brace and/or belt 200 will now be described in more detail in connection with at least FIGS. 2-11, wherein like reference numerals designate the same or corresponding parts throughout the several views. Brace 200 is configured to provide pelvic-sacral support, reduced motion of SI joint(s) 130*a*, 130*b* and reduced SI joint pain.

Figure 2:
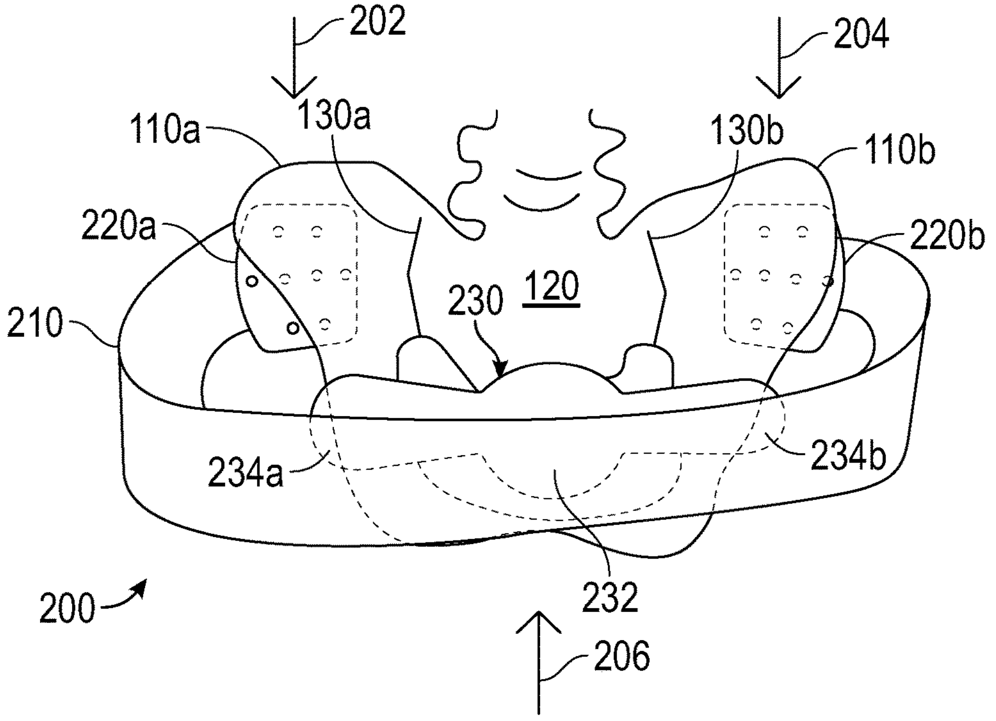
FIG. 2 illustrates a wireframe diagram showing anterior and posterior directions of force and/or support provided by one or more portions of a sacroiliac orthosis, in accordance with some embodiments.
Figure 3:
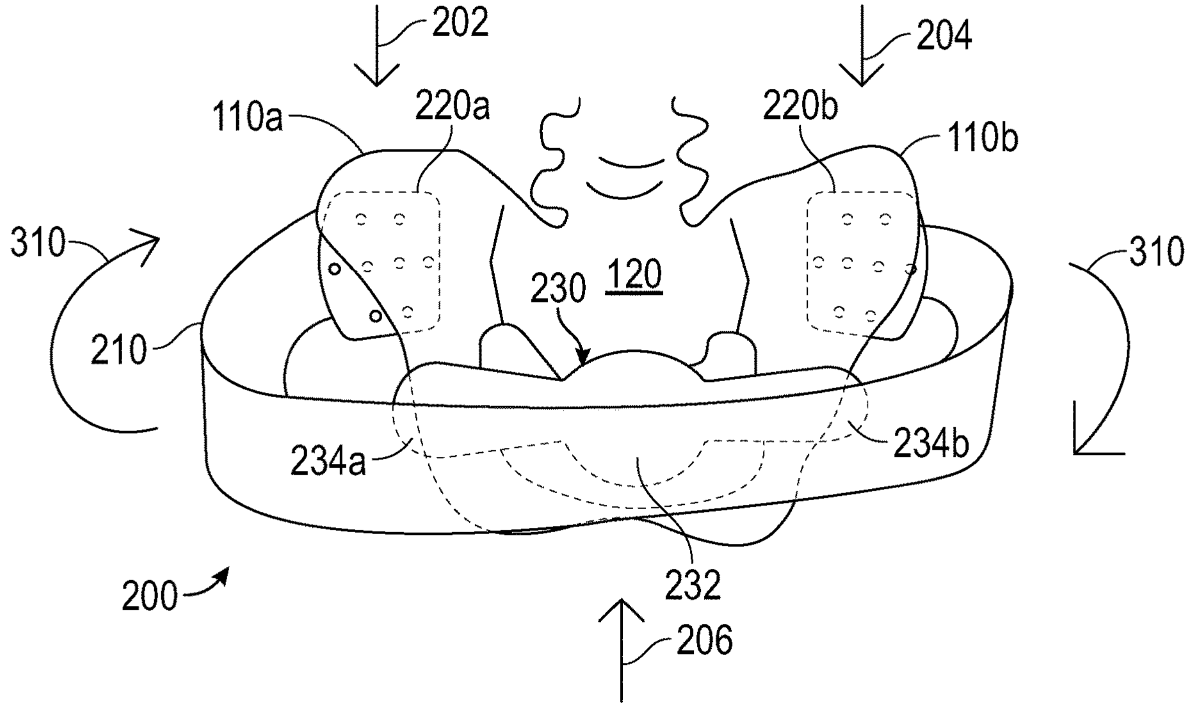
FIG. 3 illustrates the wireframe diagram of FIG. 2 with additional circumferential directions of force and/or support provided by one or more portions of a sacroiliac orthosis, in accordance with some embodiments.

FIGS. 2 and 3 illustrate wireframes of portions of a sacroiliac orthosis, brace and/or belt 200 in an appropriate alignment with portions of the hip region of a user. Brace 200 comprises a belt portion 210 and a plurality of rigid and/or semi-rigid panels 220*a*, 220*b*, 230 that are configured to apply pressure in the coronal plane of a user as belt portion 210 is cinched or tightened circumferentially around the user's pelvis and/or low back. In some embodiments, one or more of panels 220*a*, 220*b*, 230 may comprise high density polyethylene (HDPE). However, the present disclosure is not so limited and one or more of panels 220*a*, 220*b*, 230 may comprise any suitably rigid or semi-rigid material. As illustrated in FIGS. 2 and 3, a first posterior sacral panel 220*a* is adjustably coupled at a position on belt portion 210 such that first posterior sacral panel 220*a* is disposed directly posterior of a first posterior side 110*a* of the ilium of a user when brace 200 is worn. A second posterior sacral panel 220*b* is adjustably coupled at a different position on belt portion 210 such that second posterior sacral panel 220*b* is disposed directly posterior of a second posterior side 110*b* of the ilium of the user when brace 200 is worn. In some embodiments, first and second posterior sacral panels 220*a*, 220*b* may have a substantially rectangular form factor, for example, having rounded corners and at least one outwardly bowed or convex side as illustrated. However, the present disclosure is not so limited and first and second sacral panels 220*a*, 220*b* may have any suitable form factor.

In some embodiments, brace 200 also comprises a rigid or semirigid, substantially flat anterior abdominal panel 230 coupled to yet another position on belt portion 210 such that anterior abdominal panel 230 is disposed directly against an anterior side of an abdomen of the user when brace 200 is worn.

When brace 200 is properly positioned and belt portion 210 is cinched around the waist, low back and/or hips of the user, brace 200 provides increased pelvic-sacral support. The adjustable pressure system formed by belt portion 210 and at least a subset of panels 220*a*, 220*b*, 230 reduces motion about and thereby stabilizes first and/or second SI joints 130*a*, 130*b*. For example, as illustrated in FIGS. 2 and 3, when belt portion 210 is tightened along its longitudinal extent (in a circumferential direction about the user's waist, hips and/or low back) a circumferential force 310 is generated about belt portion 210. This causes posterior sacral panels 220*a*, 220*b* to be pressed in an anterior direction (denoted by respective arrows 202, 204) and apply a respective force to first and second posterior sides 110*a*, 110*b* of ilium of the pelvis in the same anterior direction. Similarly, anterior abdominal panel 230 is pressed in a posterior direction (denoted by arrow 206) and applies a force to the abdomen of the user in the same posterior direction.

As can be seen in FIGS. 2 and 3, while each of first and second posterior sacral panels 220*a*, 220*b* ultimately provide an anterior force to respective posterior sides of the ilium, to optimize SI joint stability, it may be desirable for abdominal panel 230 to provide this posterior force across a relatively broader area of the abdomen directly anterior of sacrum 120, SI joints 130*a*, 130*b*, and at least a portion of first and second sides 110*a*, 110*b* of the ilium. Accordingly, in some embodiments, abdominal panel 230 has a substantially "plus", "cross", or "batman emblem"-like shape. For example, in some such embodiments, abdominal panel 230 comprises a central portion 232 and a first and a second extension 234*a*, 234*b*, each extending away from central portion 232 in opposite directions. Central portion 232 may have an enlarged, substantially circular or ellipsoid form factor such that central portion 232 bulges with respect to the immediately adjacent portions of first and second extensions 234*a*, 234*b*. Such an enlarged form factor allows central portion 232 to distribute a portion of the posterior force across a relatively broader portion of the abdomen directly overlying at least sacrum 120. Similarly, in some embodiments, first and second extensions 234*a*, 234*b* may increase in width along their lengths of extension away from central portion 232. Such a form factor allows first and second extensions 234*a*, 234*b* to distribute a portion of the posterior force across a relatively broader portion of the abdomen directly anterior of respective SI joints 130*a*, 130*b* and at least portions of first and second sides 110*a*, 110*b* of ilium along its length of extension. In this way, belt portion 210, posterior sacral panels 220*a*, 220*b* and, in some embodiments, anterior abdominal panel 230 work together to apply circumferential forces 310, posterior forces 202, 204 and distributed anterior force 206 to, thereby, stabilize and increase support to SI joints 130*a*, 130*b*, specifically.

Figure 4A:
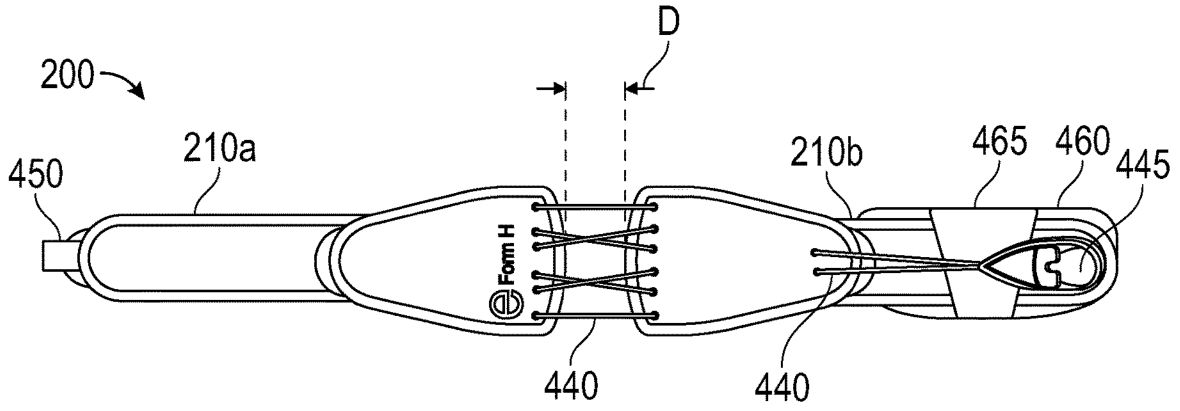
FIG. 4A illustrates an outer view of a sacroiliac orthosis, in accordance with some embodiments.
Figure 4B:
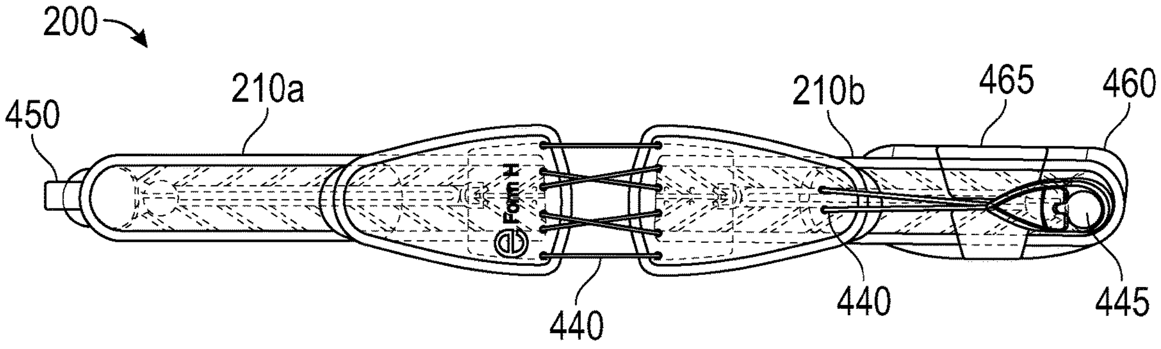
FIG. 4B illustrates a semi-transparent outer view of the sacroiliac orthosis of FIG. 4A providing partial visibility of one or more inner features of the sacroiliac orthosis.
Figure 5A:
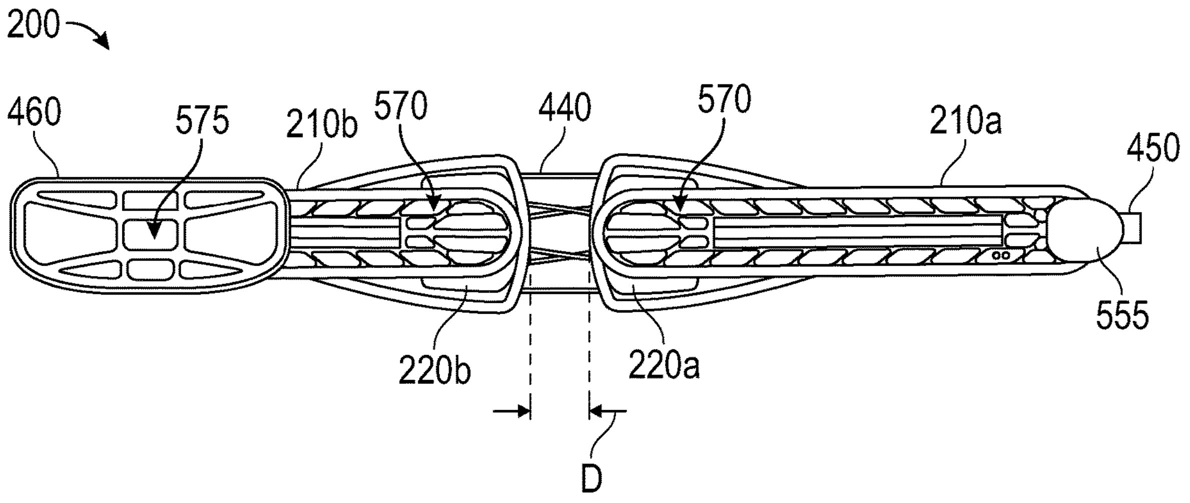
FIG. 5A illustrates an inner view of the sacroiliac orthosis of FIGS. 4A and 4B, in accordance with some embodiments.
Figure 5B:
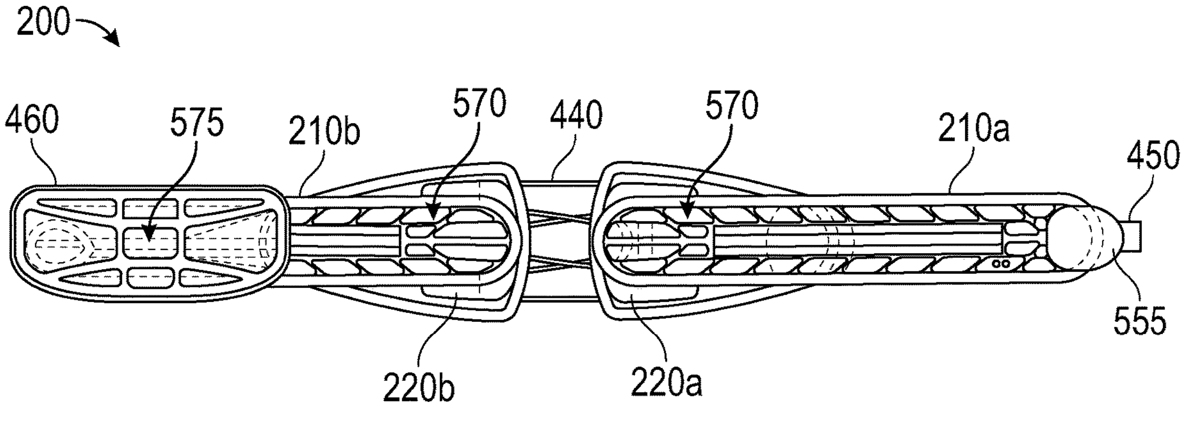
FIG. 5B illustrates a semi-transparent inner view of the sacroiliac orthosis of FIG. 5A providing partial visibility of one or more outer features of the sacroiliac orthosis.
Figure 6A:
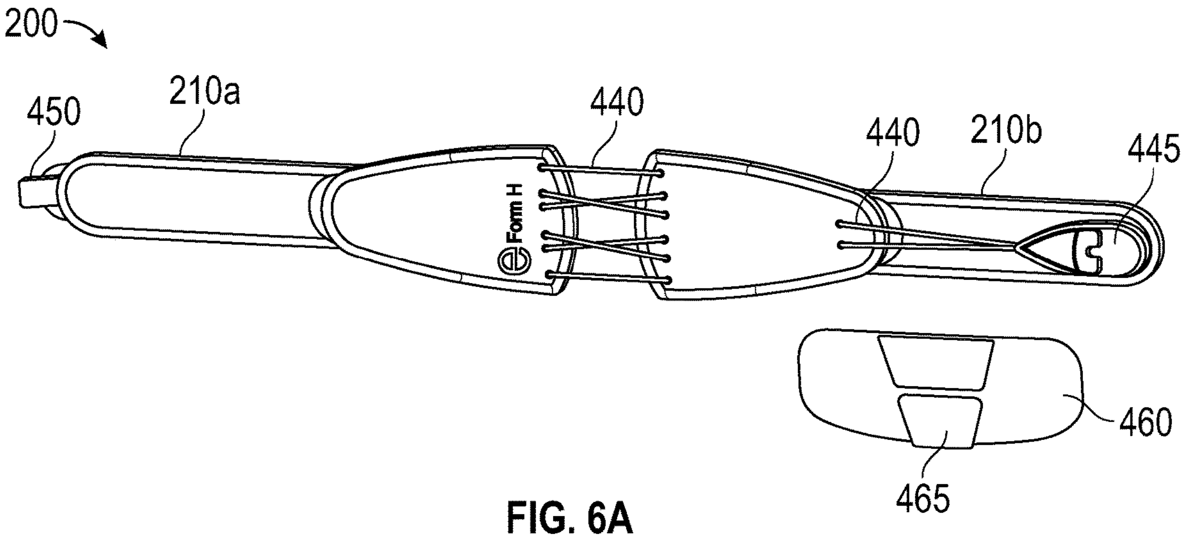
FIG. 6A illustrates an outer view of a sacroiliac orthosis having a removable anterior abdominal panel, in accordance with some embodiments.
Figure 6B:
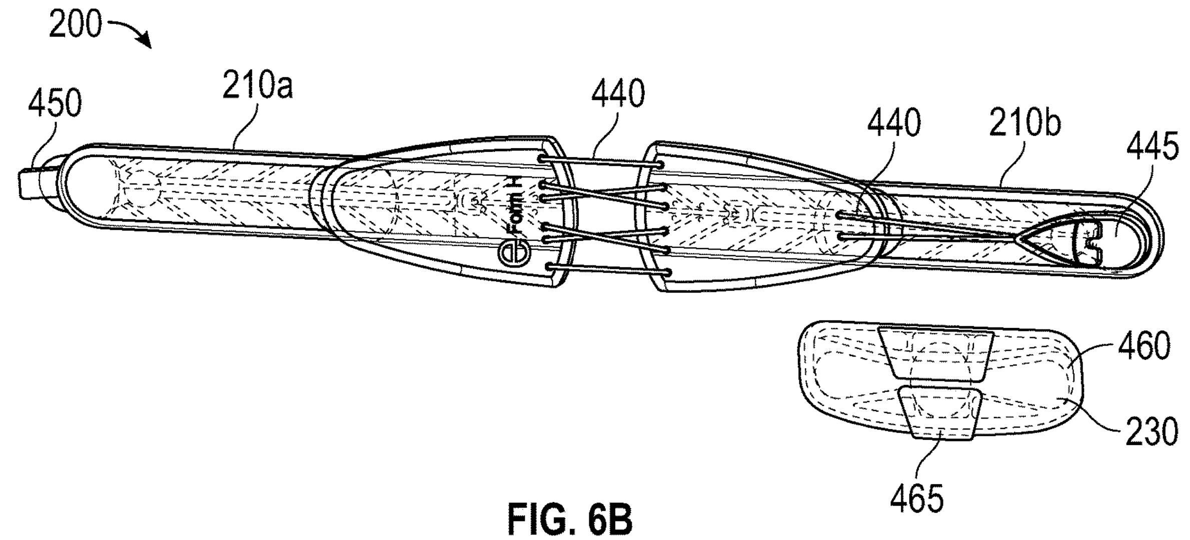
FIG. 6B illustrates a semi-transparent outer view of the sacroiliac orthosis of FIG. 6A providing partial visibility of one or more inner features of the sacroiliac orthosis.
Figure 7A:
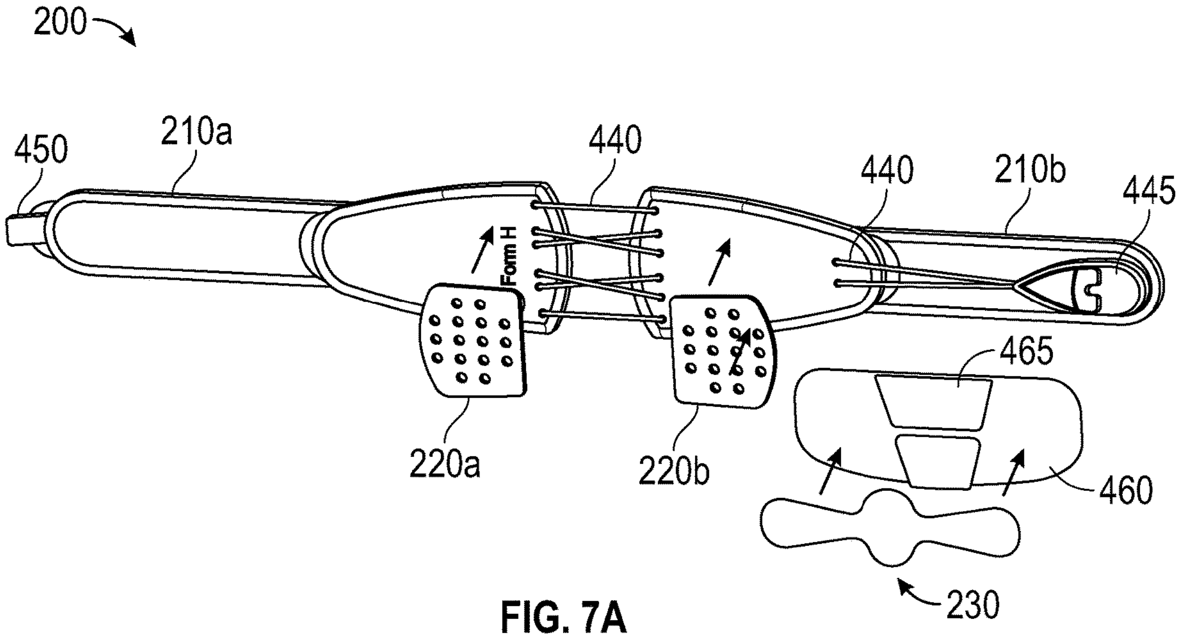
FIG. 7A illustrates an outer view of a sacroiliac orthosis with supportive plates removed therefrom, in accordance with some embodiments.
Figure 7B:
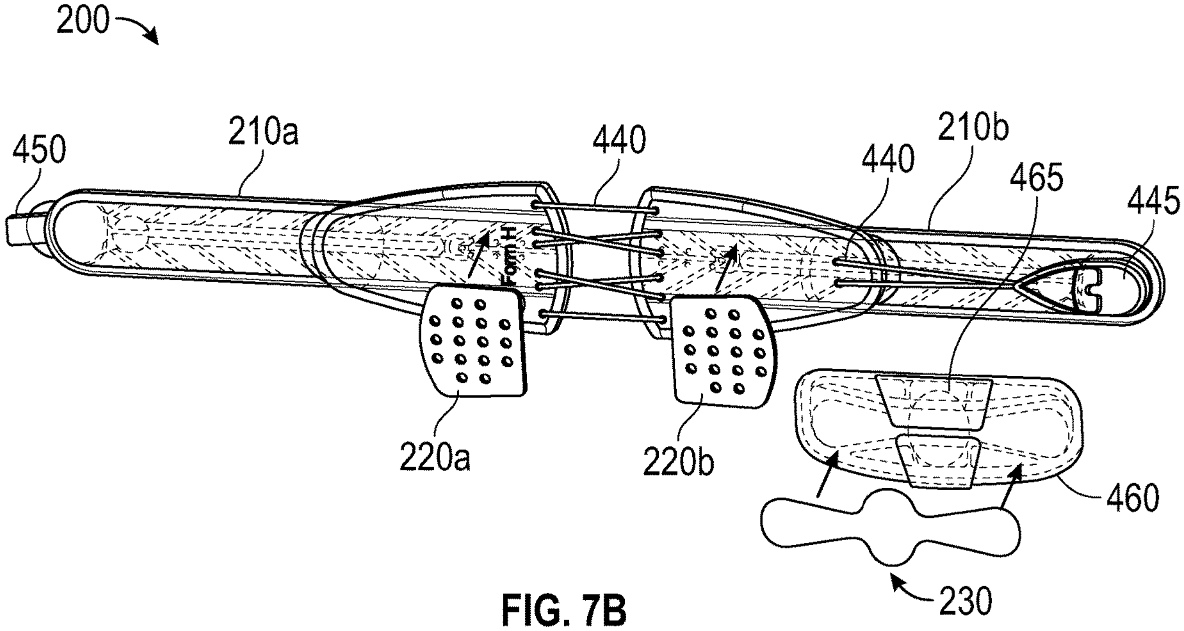
FIG. 7B illustrates a semi-transparent outer view of the sacroiliac orthosis of FIG. 7A providing partial visibility of one or more inner features of the sacroiliac orthosis.
Figure 8:
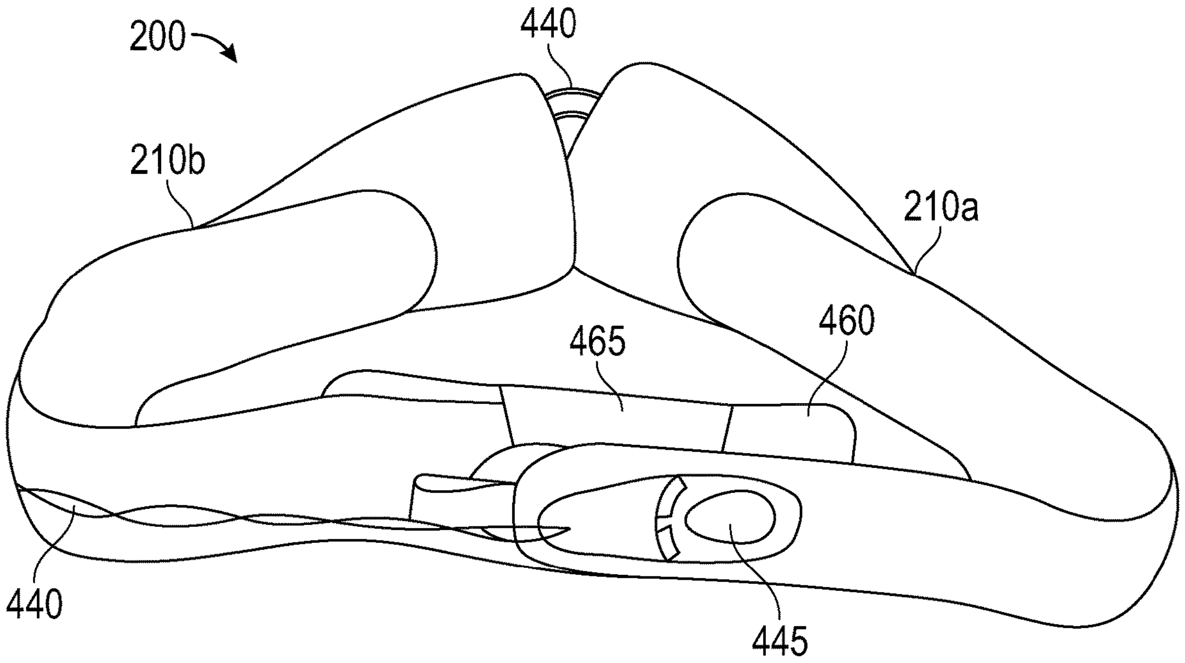
FIG. 8 illustrates a perspective wireframe view of a sacroiliac orthosis having ends of its belt portion coupled to one another, in accordance with some embodiments.
Figure 9:
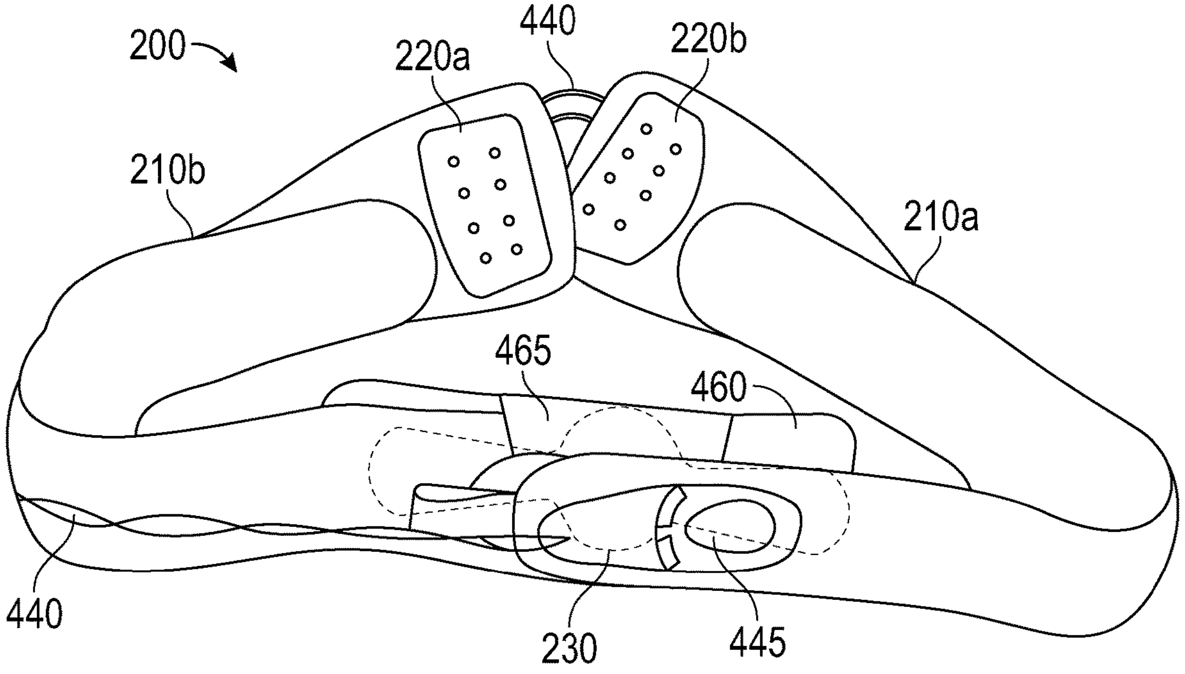
FIG. 9 illustrates a position of supportive panels within the wireframe view of the sacroiliac orthosis of FIG. 8, in accordance with some embodiments.

Several detailed aspects of one or more embodiments of brace 200 will now be described in connection with one or more of FIGS. 4A-11. FIGS. 4A, 4B, 6A, 6B, 7A and 7B illustrate an outer side of brace 200. FIGS. 4A and 4B illustrate brace 200 with a removable anterior abdominal panel housing 460 attached to belt portion 210. FIGS. 6A and 6B illustrate brace 200 with removable anterior abdominal panel housing 460 detached from belt portion 210. FIGS. 7A and 7B illustrate semi exploded views of brace 200 with removable anterior abdominal panel housing 460 detached from belt portion 210 and panels 220*a*, 220*b*, 230 outside of belt portion 210. FIGS. 5A and 5B illustrate an inner side of brace 200. And FIGS. 8-11 illustrate various views or wireframe illustrations of brace 200 with the second ends of belt portions 220*a*, 220*b* attached to one another.

To affect cinching and/or tightening of belt portion 210 along its longitudinal extent, in some embodiments, belt portion 210 can comprise a first belt portion 210*a* and a second belt portion 210*b*. In some embodiments, first and second belt portions 210*a*, 210*b* are adjustably coupled to one another at respective first ends via a closure system. As illustrated, the closure system may include a plurality of laces 440; however, it will be appreciated by a skilled artisan that any number of conventional orthotic closure systems may be employed. In some of the embodiments where the closure system includes laces 440, laces 440 are configured to provide a predetermined spacing "D" (see FIGS. 4A and 5A) between the adjacent and facing first ends of first and second belt portions 210*a*, 210*b*. In some other embodiments, laces 440 are configured to provide an adjustable spacing "D" between the adjacent and facing first ends of first and second belt portions 210*a*, 210*b* (see FIGS. 4A and 5A).

In some embodiments, laces 440 may be strung back and forth between the adjacent and facing first ends of first and second belt portions 210*a*, 210*b* a plurality of times utilizing any suitable features, for example, hooks, loops and/or apertures in one or more portions of first and second belt portions 210*a*, 210*b*. For example, the outermost passes of laces 440 may extend between the adjacent and facing first ends of first and second belt portions 210*a*, 210*b* along a path that is substantially parallel to the longitudinal extent of belt portions 210*a*, 210*b*; while the innermost passes of laces 440 may extend between the adjacent and facing first ends of first and second belt portions 210*a*, 210*b* along paths that are askew from the direction substantially parallel to the longitudinal extent of belt portions 210*a*, 210*b* such that passes in pairs of the innermost passes of laces 440 cross one another in a substantially X-shaped pattern. Employing both types of run extensions of laces 440 between the adjacent and facing first ends of first and second belt portions 210*a*, 210*b* provides both increased cinching ability as well as increased resistance to misalignment between first and second belt portions 210*a*, 210*b* when cinched.

In some embodiments, at least a portion of laces 440 may ultimately extend along a portion of second belt portion 210*b* and attach to an adjustment mechanism 445, for example a pull-tab, configured to adjust the spacing "D" between the adjacent and facing first ends of first and second belt portions 210*a*, 210*b*. For example, adjustment mechanism 445 may be configured to decrease the spacing "D" when pull tab 445 is pulled away from the user's body while brace 200 is at least partially secured around the user. In some embodiments, pull tab 445 may be positioned proximate a second end of second belt portion 210*b* opposite the first end. However, the present disclosure is not so limited and pull tab 445 may be disposed at any suitable location on brace 200. In operation, upon coupling of the second ends of first and second belt portions 210*a*, 210*b* to one another around the user's waist, pull tab 445 may be pulled until the desired spacing "D" between the adjacent and facing first ends of first and second belt portions 210*a*, 210*b* and circumferential force 310 is achieved. Then pull tab 445 may be secured to second belt portion 210*b*, for example, via hook and loop fasteners.

Adjusting pull-tab 445 has the effect of potentially providing two simultaneous adjustments to brace 200. First, it adjusts the spacing "D" between the adjacent and facing first ends of first and second belt portions 210*a*, 210*b*. Because, as will be described in more detail, first and second posterior sacral panels 220*a*, 220*b* are embedded in and/or otherwise secured proximate to the first ends of first and second belt portions 210*a*, 210*b*, adjusting the spacing "D" between the adjacent and facing first ends of first and second belt portions 210*a*, 210*b* also adjusts a related spacing between first and second posterior sacral panels 220*a*, 220*b*. This allows for customization of brace 200 to the specific morphologies of the user. Second, if the second ends of first and second belt portions 210*a*, 210*b* are already coupled to one another around a user's waist, adjusting pull-tab 445 will also have the secondary effect of simultaneously adjusting circumferential tension 310 (see FIG. 3) in belt portions 210*a*, 210*b*. Since this adjustment of circumferential tension 310 is directly related to the adjustment in the spacing "D", their mutual adjustments are linked.

In some embodiments, first and second belt portions 210*a*, 210*b* are additionally or alternatively adjustably coupled to one another at respective second ends via fastening straps 555 (see, FIGS. 5A, 5B), e.g., hook and loop fastening straps. In some embodiments, at least a portion of the second ends of each of first and second belt portions 210*a*, 210*b* themselves may comprise such fastening straps and may include complementary hook and loop materials configured to overlap one another and secure first and second belt portions 210*a*, 210*b* together. In some embodiments, one or both ends of the fastening straps 555 comprise a gripping feature 450 (e.g., pull tabs, loops or other suitable mechanisms) that allow the user to grasp first and second belt portions 210*a*, 210*b* and adjust an amount of circumferential tension 310 by controlling the degree of overlap between the second ends of first and second belt portions 210*a*, 210*b*, thereby adjusting an amount of force 202, 204, 206, pressure and stabilizing support provided to SI joints 130*a*, 130*b*.

As briefly described above, first and second posterior sacral panels 220*a*, 220*b* may be embedded, secured or sewn into a pocket within, and/or otherwise secured proximate to, the first ends of first and second belt portions 210*a*, 210*b* (see, e.g., FIGS. 5A, 5B, 7A and 7B). In some embodiments, first and second posterior sacral panels 220*a*, 220*b* are removably embedded in and/or otherwise secured to first ends of first and second belt portions 210*a*, 210*b*. This removability may aid in cleaning or washing of brace 200. In some other embodiments, first and second posterior sacral panels 220*a*, 220*b* are permanently embedded in or sewn into a pocket of, and/or otherwise secured to, first and second belt portions 210*a*, 210*b*. Such permanent securement may aid in preventing loss or misplacement of panels 220*a*, 220*b*.

In some embodiments, an inner, user-facing surface 570 of belt portions 210*a*, 210*b* may be textured and/or patterned to reduce slippage or drifting of belt portions 210*a*, 210*b* while brace 200 is worn. For example, as illustrated in FIGS. 5A and 5B, surface 570 may have a raised or textured pattern that is substantially symmetrical about a midline extending along a length of extension of belt portions 210*a*, 210*b*; in some such embodiments and for further example, raised or textured portions of surface 570 symmetrically skewing centrally toward the spacing "D" between belt portions 210*a*, 210*b* toward its lateral extents.

In some embodiments, brace 200 comprises anterior abdominal panel housing 460, which is configured to house and/or secure anterior abdominal panel 230 therein (see, e.g., FIG. 6B). In some embodiments, abdominal panel housing 460 comprises a thermoformed foam, formed to have a void substantially in the shape of anterior abdominal panel 230. However, the present disclosure is not so limited and abdominal panel housing 460 may comprise any suitable material.

In some embodiments, anterior abdominal panel housing 460 is permanently attached, e.g., sewn, to one of belt portions 210*a*, 210*b*. In some other embodiments, anterior abdominal panel housing 460 is removably attached to one of belt portions 210*a*, 210*b*, e.g., second belt portion 210*b* as illustrated in FIGS. 4A and 4B. Abdominal panel housing 460 may be removably attached to one of belt portions 210*a*, 210*b* via a fixing mechanism 465, e.g., hook and loop fasteners, a clip, a strap, a band, a loop, an elastic member, a buckle, or any other suitably adjustable fixing mechanism. In some embodiments, such removable attachment aids in proper placement and adjustment of abdominal panel housing 460 against the abdomen of variously sized and shaped users. For example, in embodiments where fixing mechanism 465 affords such a sliding degree of freedom, abdominal panel housing 460 may be slid along the one of belt portions 210*a*, 210*b* to which it is attached until abdominal panel housing 460 is properly positioned. This may be particularly useful where cinching belt portions 210*a*, 210*b* around the waist of the user results in misalignment of abdominal panel housing 460 that was initially roughly properly aligned. In embodiments where fixing mechanism 465 does not afford such a sliding degree of freedom (e.g., embodiments where fixing mechanism 465 comprises hook and loop fasteners), abdominal panel housing 460 may be properly fixed to one of belt portions 210*a*, 210*b*. In some embodiments, an inner, user-facing side of abdominal panel housing 460 may have a textured and/or patterned surface 575 configured to reduce slippage or drifting of abdominal panel housing 460 while brace 200 is worn.

While embodiments of brace 200 have been described including anterior abdominal panel housing 460 and anterior abdominal panel 230, brace 200 may still be at least partially functional without the use of anterior abdominal panel housing 460 and anterior abdominal panel 230 disposed therein. For example, belt portions 210*a*, 210*b* may still be configured to provide sufficient force and pressure against the user's abdomen to suitably stabilize and support SI joints 130*a*, 130*b*, as described above, provided they are cinched tightly enough to provide sufficient circumferential force 310 and, so, anterior force 206.

Figure 10:
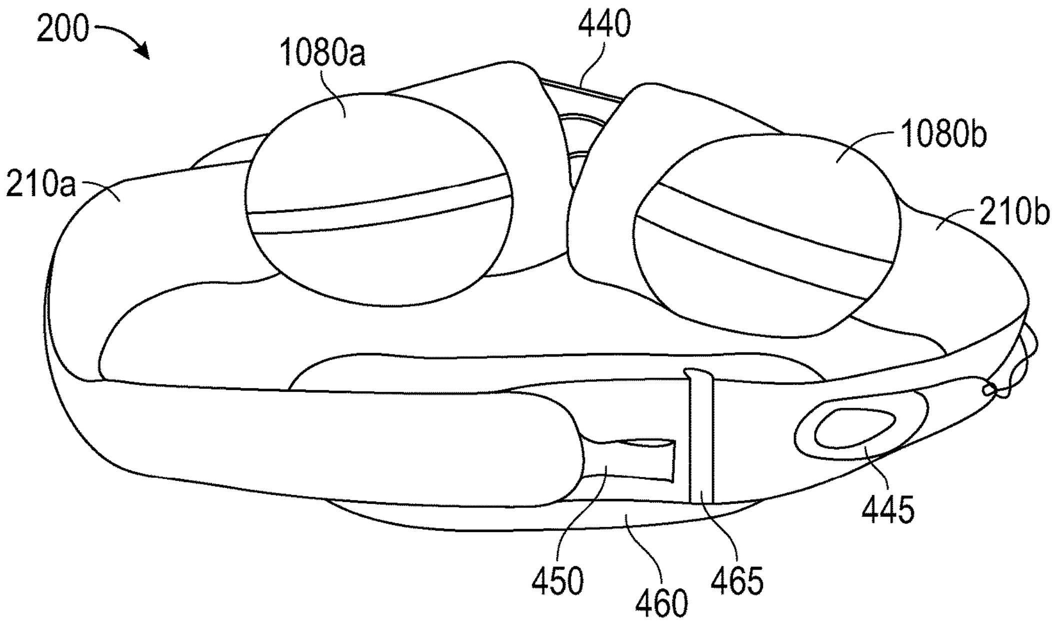
FIG. 10 is a wireframe illustration of a substantially anterior view of a sacroiliac orthosis, in accordance with some example embodiments.
Figure 11:
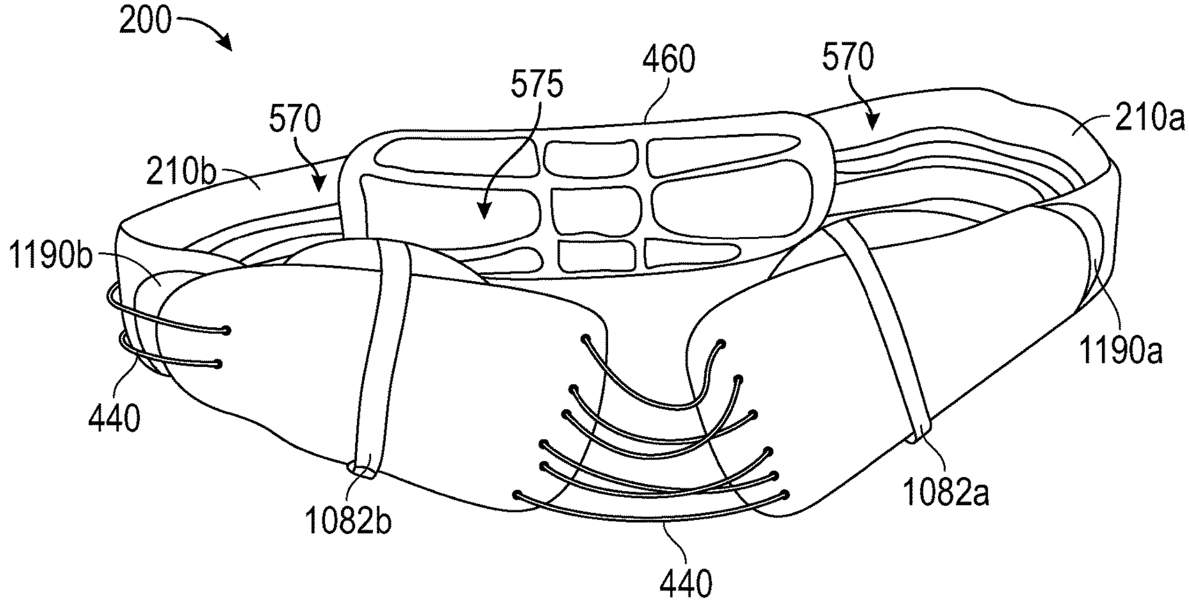
FIG. 11 is a wireframe illustration of a substantially posterior view of the sacroiliac orthosis of FIG. 10, in accordance with some example embodiments.

As further illustrated at least in FIGS. 10 and 11, brace 200 may optionally include pads 1080*a*, 1080*b*, configured to provide added cushion and a more flexible fit, particularly when disposed on belt portions 210*a*, 210*b* between the user's hips and first and second posterior sacral panels 220*a*, 220*b*. In some embodiments, pads 1080*a*, 1080*b* are configured to be removable, for example, attached utilizing hook and loop fasteners or one or more elastic bands 1082*a* (see FIG. 11) without taking away the structural support afforded to brace 200 by posterior sacral panels 220*a*, 220*b* and, optionally, anterior abdominal panel 230. In some other embodiments, pads 1080*a*, 1080*b* are permanently secured, e.g., sewn, to belt portions 210*a*, 210*b*.

As further illustrated by at least FIGS. 10 and 11, in some embodiment, first ends of first and second belt portions 210*a*, 210*b* may be pivotally coupled to the remainder of their corresponding belt portions 210*a*, 210*b* via respective pivoting fixtures 1190*a*, 1190*b*. In some such embodiments, pivoting fixtures 1190*a*, 1190*b* may be sewn into, or otherwise coupled to, the first ends and remainders of first and second belt portions 210*a*, 210*b*. Accordingly, in such embodiments, the user is afforded an additional degree of flexibility in that first ends of first and second belt portions 210*a*, 210*b* may extend in slightly different directions than the remainder of their respective belt portions 210*a*, 210*b*, as necessitated by the features and contours of the user's unique body—for example in the case where a user has a pendulous abdomen. In some other embodiments, the first ends of first and second belt portions 210*a*, 210*b* may be non-pivotally coupled to the remainder of their corresponding belt portions 210*a*, 210*b*. In other words, the first ends of first and second belt portions 210*a*, 210*b* may be fixedly coupled to, and not be configured to pivot with respect to, the remainder of their corresponding belt portions 210*a*, 210*b* beyond that afforded by the intrinsic flexibility of the material(s) or fabric(s) comprising the fixedly coupled first ends and remainders of belt portions 210*a*, 210*b*.

In some embodiments, brace 200 can comprise further design features configured to accommodate a pendulous abdomen. In some embodiments, brace 200 can be prefabricated and, thereby, provide an off-the-shelf solution to reduce motion, pain or discomfort about the SI joints 130*a*, 130*b*, and/or damage that can result therefrom.

Example Method(s) of Use

Figure 12:
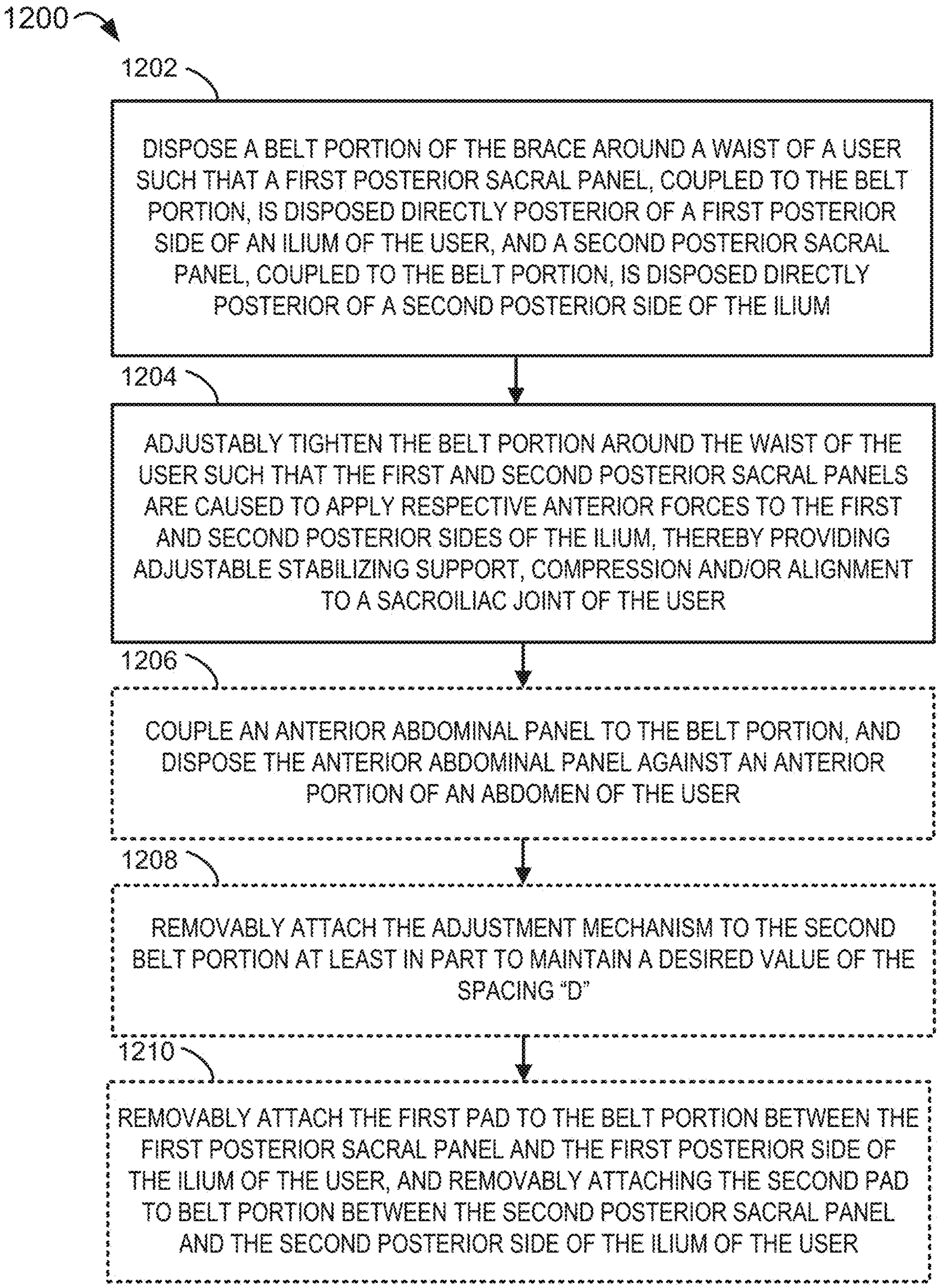
FIG. 12 is a flowchart related to a method of using a sacroiliac orthosis, in accordance with some example embodiments.

The disclosure now turns to FIG. 12, which illustrates a flowchart 1200 related to an example method of utilizing a sacroiliac orthosis, brace and/or belt to provide pelvic sacral support, as described anywhere in this disclosure.

Although the method(s) disclosed herein comprise(s) one or more steps or actions for achieving the described method (s), such steps and/or actions may be interchanged with one another, and/or a subset of these steps and/or actions may be used, without departing from the scope of the claims. In other words, unless a specific order of steps or actions is specified, the order and/or use of specific steps and/or actions may be modified without departing from the scope of the claims. One or more additional steps not specifically described herein may also be included.

Step 1202 includes disposing a belt portion of the brace around a waist of a user such that a first posterior sacral panel, coupled to the belt portion, is disposed directly posterior of a first posterior side of an ilium of the user, and a second posterior sacral panel, coupled to the belt portion, is disposed directly posterior of a second posterior side of the ilium.

For example, as previously described in connection with at least one of FIGS. 2-11, belt portion 210 of brace 200 can be disposed around a waist of a user such that first posterior sacral panel 220*a*, coupled to belt portion 210, is disposed directly posterior of first posterior side 110*a* of an ilium of the user, and second posterior sacral panel 220*b*, coupled to belt portion 210, is disposed directly posterior of second posterior side 110*b* of the ilium.

Step 1204 includes adjustably tightening the belt portion around the waist of the user such that the first and second posterior sacral panels are caused to apply respective anterior forces to the first and second posterior sides of the ilium, thereby providing adjustable stabilizing support, compression and/or alignment to a sacroiliac joint of the user.

For example, as previously described in connection with at least one of FIGS. 2-11, belt portion 210 can be adjustably tightening around the waist of the user such that first and second posterior sacral panels 220*a*, 220*b* are caused to apply respective anterior forces 202, 204 to first and second posterior sides 110*a*, 110*b* of the ilium, thereby providing adjustable stabilizing support, compression and/or alignment to sacroiliac joint(s) 130*a*, 130*b* of the user.

In some embodiments, an optional step 1206 may include coupling an anterior abdominal panel to the belt portion, and disposing the anterior abdominal panel against an anterior portion of an abdomen of the user.

For example, as previously described in connection with at least one of FIGS. 2-11, anterior abdominal panel 230 may be coupled to belt portion 210 and disposed against an anterior portion of an abdomen of the user.

In some embodiments, adjustably tightening belt portion 210 causes anterior abdominal panel 230 to apply posterior force 206 to the abdomen of the user, thereby contributing to the adjustable stabilizing support, compression and/or alignment to sacroiliac joint(s) 130*a*, 130*b* of the user.

In some embodiments, coupling anterior abdominal panel 230 to belt portion 210 comprises coupling anterior abdominal housing 460, which holds anterior abdominal panel 230, to belt portion 210, and disposing anterior abdominal panel 230 against the anterior portion of the abdomen of the user comprises disposing anterior abdominal housing 430, which holds anterior abdominal panel 230, to the anterior portion of the abdomen of the user.

In some embodiments, a user-facing surface 575 of the anterior abdominal housing is textured and/or patterned to reduce slippage or drifting of anterior abdominal housing 460 while brace 200 is worn. In some embodiments, anterior abdominal panel 230 is substantially flat and rigid or semi-rigid. In some embodiments, anterior abdominal panel 230 comprises a central portion 232 and first and second extensions 234*a*, 234*b*, which each extend away from central portion 32 in opposite directions, and central portion 232 comprises an enlarged, substantially circular or ellipsoid form factor such that central portion 232 bulges with respect to immediately adjacent portions of first and second extensions 234*a*, 234*b*. In some embodiments, for each of first and second extensions 234*a*, 234*b*, a respective width of the extension increases as the extension extends away from central portion 232. In some embodiments, central portion 232 is configured to be disposed directly anterior of at least sacrum 120 of the user when brace 200 is worn. In some embodiments, each of first and second extensions 234*a*, 234*b* are configured to be disposed directly anterior of a respective sacroiliac joint 130*a*, 130*b* and at least a portion of the corresponding one of first and second sides 110*a*, 110*b* of the ilium of the user when brace 200 is worn.

In some embodiments, belt portion 210 comprises a first belt portion 210*a*, a second belt portion 210*b*, and a plurality of laces 440 that couple adjacent and facing first ends of the first and second belt portions with an adjustable spacing (D) therebetween. First posterior sacral panel 220*a* is coupled proximate to the first end of first belt portion 210*a* and second posterior sacral panel 220*b* is coupled proximate to the first end of second belt portion 210*b*. In some embodiments, first and second posterior sacral panels 220*a*, 220*b* are permanently secured within respective pockets disposed proximate to the first end of the corresponding first and second belt portions 210*a*, 210*b*. In some embodiments, first and second posterior sacral panels 220*a*, 220*b* are removably secured proximate to the first end of the corresponding first and second belt portions 210*a*, 210*b* before brace 200 is worn by the user. In some embodiments, first and second posterior sacral panels 220*a*, 220*b* have substantially rectangular form factors. In some embodiments, first and second posterior sacral panels 220*a*, 220*b* have rounded corners and at least one outwardly bowed or convex side. In some embodiments, first and second posterior sacral panels 220*a*, 220*b* are rigid or semi-rigid.

In some embodiments, first and second belt portions 210*a*, 210*b* comprise fastening straps 450 at respective second ends and adjustably tightening belt portion 210 around the waist of the user comprises adjusting an amount of tension in belt portion 210 based at least in part on an amount of overlap between the second ends of first and second belt portions 210*a*, 210*b*. In some embodiments, fastening straps 450 comprise one or more gripping features 450 and adjustably tightening belt portion 210 around the waist of the user comprises grasping gripping feature 450 while adjusting the amount of overlap between the second ends of first and second belt portions 210*a*, 210*b*.

In some embodiments, plurality of laces 440 extend between the adjacent and facing first ends of first and second belt portions 20*a*, 210*b* a plurality of times, thereby forming a plurality of passes of the plurality of laces. In some embodiments, a first subset of the plurality of passes of laces 440 extend between the adjacent and facing first ends of first and second belt portions 210*a*, 210*b* along a path that is substantially parallel to a longitudinal extent of first and second belt portions 210*a*, 210*b*, and a second subset of the plurality of passes of laces 440 extend between the adjacent and facing first ends of first and second belt portions 210*a*, 210*b* along paths that are askew from the longitudinal extent of first and second belt portions 20*a*, 210*b* such that passes in pairs of the second subset of the plurality of passes cross one another in a substantially X-shaped pattern.

In some embodiments, at least a portion of laces 440 extend along a portion of second belt portion 210*b* and attach to adjustment mechanism 445. In some embodiments, adjustment mechanism 445 comprises a pull tab and adjustably tightening belt portion 210 around the waist of the user comprises pulling pull tap 445 away from the user's body to decrease the spacing "D" while brace 200 is at least partially secured around the user. In some embodiments, pull tab 445 is configured to simultaneously increase an amount of circumferential tension 310 in first and second belt portions 210*a*, 210*b* when pull tab 445 is pulled away from the user's body while brace 200 is at least partially secured around the user. In some embodiments, pull tab 445 is configured to simultaneously decrease a spacing between first and second posterior sacral panels 220*a*, 220*b* when pull tab 445 is pulled away from the user's body while brace 200 is at least partially secured around the user.

In some embodiments, an optional step 1208 may include removably attaching the adjustment mechanism to the second belt portion at least in part to maintain a desired value of the spacing "D". For example, as previously described in connection with at least FIGS. 2-11, adjustment mechanism 445 may be removably attached to second belt portion 210*b* at least in part to maintain a desired value of the spacing "D".

In some embodiments, the first end of each of first and second belt portions 210*a*, 210*b* is pivotally coupled to a remainder of the respective first and second belt portion 20*a*, 210*b* by a respective pivoting fixture 1190*a*, 1190*b* such that the first end of each of first and second belt portions 210*a*, 210*b* is configured to extend in slightly different direction than the remainder of the respective belt portion 210*a*, 210*b* when brace 200 is worn. In some embodiments, a user-facing surface 570 of first and second belt portions 210*a*, 210*b* is textured and/or patterned to reduce slippage or drifting of first and second belt portions 210*a*, 210*b* while brace 200 is worn. In some embodiments, the texture and/or pattern of user-facing surface 570 is substantially symmetrical about a midline extending along a length of extension of first and second belt portions 210*a*, 210*b*.

In some embodiments, an optional step 1210 may include removably attaching the first pad to the belt portion between the first posterior sacral panel and the first posterior side of the ilium of the user, and removably attaching the second pad to belt portion between the second posterior sacral panel and the second posterior side of the ilium of the user.

For example, as previously described in connection with at least one of FIGS. 2-11, first pad 1080*a* may be removably attached to belt portion 210*a* between first posterior sacral panel 220*a* and first posterior side 110*a* of the ilium of the user, and second pad 1080*b* may be removably attached to belt portion 210*b* between second posterior sacral panel 220*b* and second posterior side 110*b* of the ilium of the user.

Example Methods of Manufacture

Figure 13:
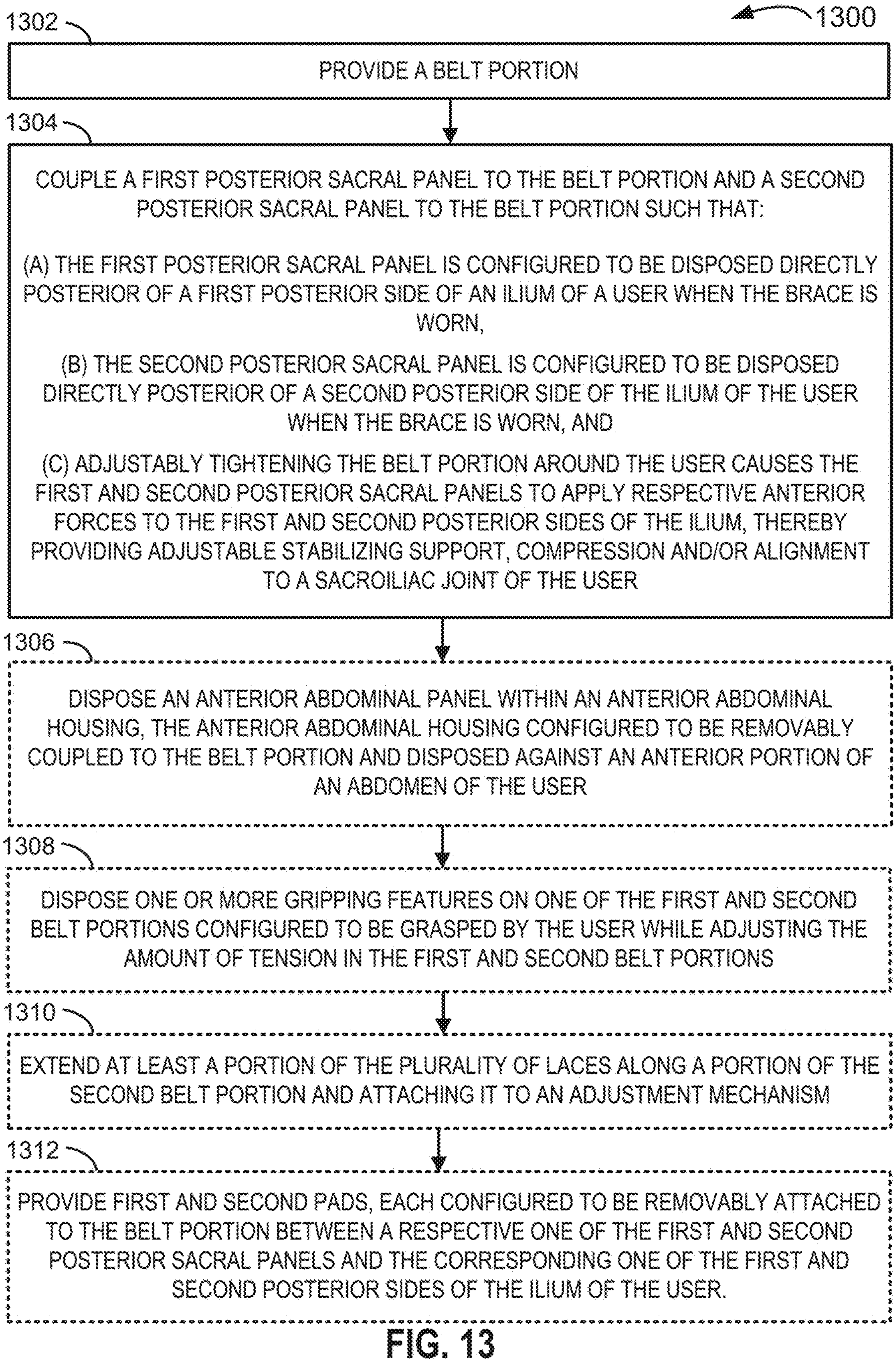
FIG. 13 is a flowchart related to a method of manufacturing a sacroiliac orthosis, in accordance with some example embodiments.

The disclosure now turns to FIG. 13, which illustrates a flowchart 1300 related to an example method of manufacturing a sacroiliac orthosis, brace and/or belt for providing pelvic sacral support, as described anywhere in this disclosure.

Although the method(s) disclosed herein comprise(s) one or more steps or actions for achieving the described method (s), such steps and/or actions may be interchanged with one another, and/or a subset of these steps and/or actions may be used, without departing from the scope of the claims. In other words, unless a specific order of steps or actions is specified, the order and/or use of specific steps and/or actions may be modified without departing from the scope of the claims. One or more additional steps not specifically described herein may also be included.

Step 1302 includes providing a belt portion. For example, as previously described in connection with at least FIGS. 2-11, belt portion 210 may be provided as described anywhere in this disclosure.

Step 1304 includes coupling a first posterior sacral panel to the belt portion and a second posterior sacral panel to the belt portion such that: (A) the first posterior sacral panel is configured to be disposed directly posterior of a first posterior side of an ilium of a user when the brace is worn, (B) the second posterior sacral panel is configured to be disposed directly posterior of a second posterior side of the ilium of the user when the brace is worn, and (C) adjustably tightening the belt portion around the user causes the first and second posterior sacral panels to apply respective anterior forces to the first and second posterior sides of the ilium, thereby providing adjustable stabilizing support, compression and/or alignment to a sacroiliac joint of the user.

For example, as previously described in connection with at least FIGS. 2-11, first posterior sacral panel 220*a* may be coupled to belt portion 210*a* and second posterior sacral panel 220*b* to belt portion 210*b* such that: (A) first posterior sacral panel 220*a* is configured to be disposed directly posterior of first posterior side 110*a* of an ilium of a user when brace 200 is worn, (B) second posterior sacral panel 220*a* is configured to be disposed directly posterior of second posterior side 110*b* of the ilium of the user when brace 200 is worn, and (C) adjustably tightening belt portion 210 around the user causes first and second posterior sacral panels 220*a*, 220*b* to apply respective anterior forces 202, 204 to first and second posterior sides 110*a*, 110*b* of the ilium, thereby providing adjustable stabilizing support, compression and/or alignment to sacroiliac joint(s) 130*a*, 130*b* of the user.

In some embodiments, an optional step 1306 may include disposing an anterior abdominal panel within an anterior abdominal housing, wherein the anterior abdominal housing is configured to be removably coupled to the belt portion and disposed against an anterior portion of an abdomen of the user. For example, as previously described in connection with at least FIGS. 2-11, anterior abdominal panel 230 may be disposed within anterior abdominal housing 460, wherein housing 460 is configured to be removably coupled to belt portion 210 and disposed against an anterior portion of an abdomen of the user.

In some embodiments, anterior abdominal panel 230 is configured to apply a posterior force 206 to the abdomen of the user, thereby contributing to the adjustable stabilizing support, compression and/or alignment to sacroiliac joint(s) 130*a*, 130*b* of the user.

In some embodiments, a user-facing surface 575 of anterior abdominal housing 460 may include a texture and/or pattern configured to reduce slippage or drifting of anterior abdominal housing 460 while brace 200 is worn.

In some embodiments, anterior abdominal panel 230 is substantially flat and rigid or semi-rigid. In some embodiments, anterior abdominal panel 230 comprises central portion 232, and first and second extensions 234*a*, 234*b* that each extend away from central portion 232 in opposite directions. In some such embodiments, central portion 232 comprises an enlarged, substantially circular or ellipsoid form factor such that central portion 232 bulges with respect to immediately adjacent portions of first and second extensions 234*a*, 234*b*. In some embodiments, for each of first and second extensions 234*a*, 234*b*, a respective width of the extension increases as the extension extends away from central portion 232. In some embodiments, anterior abdominal panel 230 is disposed within anterior abdominal housing 460 such that central portion 230 of anterior abdominal panel 230 is disposed directly anterior of at least sacrum 120 of the user when brace 200 is worn. In some embodiments, anterior abdominal panel 230 is disposed within anterior abdominal housing 460 such that each of first and second extensions 234*a*, 234*b* is disposed directly anterior of a respective sacroiliac joint 130*a*, 130*b* and at least a portion of the corresponding one of first and second sides 110*a*, 110*b* of the ilium of the user when brace 200 is worn.

In some embodiments, providing belt portion 210 comprises providing first belt portion 210*a*, providing second belt portion 210*b*, and coupling adjacent and facing first ends of first and second belt portions 210*a*, 210*b* with the adjustable spacing "D" therebetween utilizing laces (440). In some such embodiments coupling first posterior sacral panel 220*a* to belt portion 210 comprises coupling first posterior sacral panel 220*a* proximal to the first end of first belt portion 210*a*, and coupling second posterior sacral panel 220*b* to belt portion 210 comprises coupling second posterior sacral panel 220*b* proximal to the first end of second belt portion 210*b*. In some embodiments, first and second posterior sacral panels 220*a*, 220*b* are permanently secured within respective pockets disposed proximate to the first end of the corresponding first and second belt portions 210*a*, 210*b*. In some embodiments, first and second posterior sacral panels 220*a*, 220*b* are removably secured proximate to the first end of the corresponding first and second belt portions 210*a*, 210*b*. In some embodiments, first and second posterior sacral panels 220*a*, 220*b* have substantially rectangular form factors. In some embodiments, first and second posterior sacral panels 220*a*, 220*b* have rounded corners and at least one outwardly bowed or convex side. In some embodiments, first and second posterior sacral panels 220*a*, 220*b* are rigid or semi-rigid.

In some embodiments, first and second belt portions 210*a*, 210*b* are each provide with a fastening strap 450 disposed at their respective second ends and configured to adjust an amount of tension in first and second belt portions 210*a*, 210*b* based at least in part on an amount of overlap between the second ends of first and second belt portions 20*a*, 210*b*.

In some embodiments, an optional step 1308 may include disposing one or more gripping features on one of the first and second belt portions, the one or more gripping features configured to be grasped by the user while adjusting the amount of tension in the first and second belt portions. For example, as previously described in connection with at least FIGS. 2-11, one or more gripping features 450 may be disposed on one of first and second belt portions 210*a*, 210*b* and configured to be grasped by the user while adjusting the amount of tension in first and second belt portions 210*a*, 210*b*.

In some embodiments, extending laces 440 between the adjacent and facing first ends of first and second belt portions 210*a*, 210*b* a plurality of times comprises: (A) extending a first subset of the plurality of passes of laces 440 between the adjacent and facing first ends of first and second belt portions 210*a*, 210*b* along a path that is substantially parallel to a longitudinal extent of first and second belt portions 210*a*, 210*b*, and (B) extending a second subset of the plurality of passes of laces 440 between the adjacent and facing first ends of first and second belt portions 210*a*, 210*b* along paths that are askew from the longitudinal extent of first and second belt portions 210*a*, 210*b* such that passes in pairs of the second subset of the plurality of passes cross one another in a substantially X-shaped pattern.

In some embodiments, an optional step 1310 may include extending at least a portion of the plurality of laces along a portion of the second belt portion and attaching the portion of the plurality of laces to an adjustment mechanism. For example, as previously described in connection with at least one of FIGS. 2-11, at least a portion of laces 440 may extend along a portion of second belt portion 210*b* and attach to adjustment mechanism 445.

In some embodiments, adjustment mechanism 445 comprises a pull tab configured to decrease the spacing "D" when pull tab 445 is pulled away from the user's body while brace 200 is at least partially secured around the user. In some embodiments, pull tab 445 is configured to simultaneously increase an amount of circumferential tension 310 in first and second belt portions 210*a*, 210*b* when pull tab 445 is pulled away from the user's body while brace 200 is at least partially secured around the user. In some embodiments, pull tab 445 is configured to simultaneously decrease a spacing between first and second posterior sacral panels 220*a*, 220*b* when pull tab 445 is pulled away from the user's body while brace 200 is at least partially secured around the user. In some embodiments, adjustment mechanism 445 is configured to be removably attached to second belt portion 210*b* at least in part to maintain a desired value of the spacing "D".

In some embodiments, providing first belt portion 210*a* comprises pivotally coupling the first end of first belt portion 210*a* to a remainder of first belt portion 210*a* utilizing a first pivoting fixture 1190*a* such that the first end of first belt portion 210*a* is configured to extend in a slightly different direction than the remainder of first belt portion 210*a* when 200 brace is worn; and providing second belt portion 210*b* comprises pivotally coupling the first end of second belt portion 210*b* to a remainder of second belt portion 210*b* utilizing a second pivoting fixture 1190*b* such that the first end of second belt portion 210*b* is configured to extend in a slightly different direction than the remainder of second belt portion 210*b* when 200 brace is worn.

In some embodiments, user-facing surface 570 of first and second belt portions 210*a*, 210*b* is textured and/or patterned to reduce slippage or drifting of first and second belt portions 210*a*, 210*b* while brace 200 is worn. In some embodiments, the texture and/or pattern of user-facing surface 570 is substantially symmetrical about a midline extending along a length of extension of first and second belt portions 210*a*, 210*b*.

In some embodiments, an optional step 1312 may include providing a first pad and a second pad, each configured to be removably attached to the belt portion between a respective one of the first and second posterior sacral panels and the corresponding one of the first and second posterior sides of the ilium of the user. For example, as previously described in connection with at least one of FIGS. 2-11, first and second pads 1080*a*, 1080*b* may be provided such that each is configured to be removably attached to belt portion 210 between a respective one of first and second posterior sacral panels 220*a*, 220*b* and the corresponding one of first and second posterior sides 110*a*, 110*b* of the ilium of the user.

Although the disclosure herein has been described with reference to particular embodiments, it is to be understood that these embodiments are merely illustrative of the principles and applications of the present disclosure. It is therefore to be understood that numerous modifications may be made to the illustrative embodiments and that other arrangements may be devised without departing from the spirit and scope of the present disclosure as defined by the appended claims.

The invention claimed is:

1. An orthopedic sacroiliac brace, comprising:
- a belt portion;
- a first posterior sacral panel coupled to the belt portion and configured to be disposed directly posterior of a first posterior side of an ilium of a user;
- a second posterior sacral panel coupled to the belt portion and configured to be disposed directly posterior of a second posterior side of the ilium; and
- a rigid anterior abdominal panel configured to be disposed against an anterior portion of an abdomen of the user and coupled to the belt portion, the rigid anterior abdominal panel comprising:
  - a rigid central portion having a substantially circular or ellipsoid form factor and configured to be disposed directly anterior of at least the sacrum of the user when the brace is worn; and
  - first and second rigid extensions that each extend away from the rigid central portion in opposite directions, wherein each of the rigid first and second extensions:
    - has a respective rounded distal end,
    - has a respective width that increases continuously along an entire respective length of extension from the rigid central portion to the respective rounded distal end, the respective length of extension being longer than a length of the respective rounded distal end, and
    - is configured to be disposed directly anterior of a respective sacroiliac joint and at least a portion of the corresponding one of a first and a second anterior side of the ilium of the user when the brace is worn; and
- wherein adjustably tightening the belt portion around the user causes the first and second posterior sacral panels to apply respective anterior forces to the first and second posterior sides of the ilium, and causes the rigid anterior abdominal panel to simultaneously apply a posterior force to the abdomen of the user, thereby providing adjustable stabilizing support, compression and/or alignment to the sacroiliac joints of the user.

2. The brace of claim 1, wherein the rigid anterior abdominal panel is disposed within an anterior abdominal housing configured to be removably or adjustably coupled to the belt portion.

3. The brace of claim 2, wherein a user-facing surface of the anterior abdominal housing is textured to reduce slippage or drifting of the anterior abdominal housing while the brace is worn.

4. The brace of claim 1, wherein the rigid anterior abdominal panel is substantially flat.

5. The brace of claim 1, wherein the belt portion comprises:
- a first belt portion;
- a second belt portion; and
- a plurality of laces that couple adjacent and facing first ends of the first and second belt portions with an adjustable spacing (D) therebetween,
- the first posterior sacral panel being coupled proximate to the first end of the first belt portion and the second posterior sacral panel being coupled proximate to the first end of the second belt portion.

6. The brace of claim 5, wherein the first and second posterior sacral panels are permanently secured within respective pockets disposed proximate to the first end of the corresponding first and second belt portions.

7. The brace of claim 5, wherein the first and second posterior sacral panels are removably secured proximate to the first end of the corresponding first and second belt portions.

8. The brace of claim 5, wherein the first and second belt portions comprise fastening straps at respective second ends configured to adjust an amount of tension in the belt portion based at least in part on an amount of overlap between the second ends of the first and second belt portions and, thereby, contribute to the adjustable stabilizing support, compression and/or alignment to the sacroiliac joint.

9. The brace of claim 8, wherein the fastening straps comprise one or more gripping features configured to be grasped by the user while adjusting the amount of tension in the first and second belt portions.

10. The brace of claim 5, wherein the plurality of laces extend between the adjacent and facing first ends of the first and second belt portions a plurality of times, thereby forming a plurality of passes of the plurality of laces.

11. The brace of claim 10, wherein:
- a first subset of the plurality of passes of the plurality of laces extend between the adjacent and facing first ends of the first and second belt portions along a path that is substantially parallel to a longitudinal extent of the first and second belt portions; and
- a second subset of the plurality of passes of the plurality of laces extend between the adjacent and facing first ends of the first and second belt portions along paths that are askew from the longitudinal extent of the first and second belt portions such that passes in pairs of the second subset of the plurality of passes cross one another in a substantially X-shaped pattern.

12. The brace of claim 10, wherein at least a portion of the plurality of laces extend along a portion of the second belt portion and attach to an adjustment mechanism.

13. The brace of claim 12, wherein the adjustment mechanism comprises a pull tab configured to decrease the spacing "D" when the pull tab is pulled away from the user's body while the brace is at least partially secured around the user.

14. A method of using an orthopedic sacroiliac brace for providing pelvic sacral support, the method comprising:

coupling a rigid anterior abdominal panel to a belt portion of the brace, the rigid anterior abdominal panel comprising:

a rigid central portion having a substantially circular or ellipsoid form factor and configured to be disposed directly anterior of at least the sacrum of a user when the brace is worn; and first and second rigid extensions that each extend away from the rigid central portion in opposite directions, wherein each of the first and second rigid extensions:

has a respective rounded distal end, and has a respective width that increases continuously along a respective length of extension from the rigid central portion to the respective rounded distal end, the respective length of extension being longer than a length of the respective rounded distal end;

disposing the belt portion of the brace around a waist of the user such that:

a first posterior sacral panel, coupled to the belt portion, is disposed directly posterior of a first posterior side of an ilium of the user, a second posterior sacral panel, coupled to the belt portion, is disposed directly posterior of a second posterior side of the ilium, the first rigid extension of the rigid anterior abdominal panel is disposed directly anterior of a first sacroiliac joint and at least a portion of a first anterior side of the ilium of the user, and the second rigid extension of the rigid anterior abdominal panel is disposed directly anterior of a second sacroiliac joint and at least a portion of a second anterior side of the ilium of the user; and adjustably tightening the belt portion around the waist of the user such that the first and second posterior sacral panels are caused to apply respective anterior forces to the first and second posterior sides of the ilium, and the rigid anterior abdominal panel is caused to simultaneously apply a posterior force to the abdomen of the user, thereby providing adjustable stabilizing support, compression and/or alignment to the first and second sacroiliac joints of the user.

* * * * *